United States Patent
Sakaniwa

(10) Patent No.: US 8,542,160 B2
(45) Date of Patent: Sep. 24, 2013

(54) MEDICAL IMAGE DIAGNOSIS APPARATUS HAVING A PLURALITY OF MONITORS

(75) Inventor: Hiroshi Sakaniwa, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1166 days.

(21) Appl. No.: 11/677,385

(22) Filed: Feb. 21, 2007

(65) Prior Publication Data

US 2007/0139298 A1 Jun. 21, 2007

Related U.S. Application Data

(63) Continuation of application No. 10/347,921, filed on Jan. 22, 2003.

(30) Foreign Application Priority Data

Jan. 22, 2002 (JP) ................................. 2002-013262

(51) Int. Cl.
*G09G 5/00* (2006.01)
(52) U.S. Cl.
USPC .......................................................... 345/1.1
(58) Field of Classification Search
None
See application file for complete search history.

(56) References Cited

U.S. PATENT DOCUMENTS

| | | | |
|---|---|---|---|
| 5,128,662 A * | 7/1992 | Failla | 345/1.3 |
| 5,892,511 A * | 4/1999 | Gelsinger et al. | 715/794 |
| 6,020,890 A | 2/2000 | Kohda | |
| 6,339,410 B1 | 1/2002 | Milner et al. | |
| 6,844,865 B2 | 1/2005 | Stasko | |
| 2002/0039084 A1 | 4/2002 | Yamaguchi | |

OTHER PUBLICATIONS

Stasko, Michael "A Multiple Screen Monitor" (Date Filed: Jan. 11, 2000) (U.S. Appl. No. 09/481,232).

* cited by examiner

*Primary Examiner* — Joseph Field
*Assistant Examiner* — Paul Gupta
(74) *Attorney, Agent, or Firm* — Oblon, Spivak, McClelland, Maier & Neustadt, L.L.P.

(57) ABSTRACT

A medical image diagnosis apparatus, comprises an image generator, a display, and a mechanism. The image generator is configured to generate a medical image. The display comprises a plurality of monitors and is configured to display the medical image. The mechanism is configured to change an arrangement of the plurality of monitors with respect to each of the monitors.

18 Claims, 16 Drawing Sheets

MEDICAL IMAGE DIAGNOSIS APPARATUS HAVING A PLURALITY OF MONITORS

CROSS-REFERENCE TO RELATED APPLICATIONS

This continuation application is based upon, and claims the benefit of priority from prior U.S. patent application Ser. No. 10/347,921, filed on Jan. 22, 2003 which claims the benefit of priority from prior Japanese Patent Application No. 2002-013262, filed Jan. 22, 2002. The entire contents of the above-identified applications are incorporated herein by reference.

FIELD OF THE INVENTION

The present invention relates to a medical image diagnosis apparatus and a display for a use in a medical image diagnosis apparatus, with a plurality of monitors to display medical images. The present invention further relates to a method of arranging such a plurality of monitors.

BACKGROUND OF THE INVENTION

Various kinds of medical diagnoses have been realized nowadays by interpreting medical images obtained from medical diagnosis apparatuses, such as, for example, an X-ray diagnosis apparatus, an X-ray CT (computer tomography) apparatus, an MRI (magnetic resonance imaging) apparatus, a nuclear medical diagnosis apparatus, an ultrasound diagnosis apparatus, and an endoscopic image apparatus. In the event that medical images are obtained from such medical diagnosis apparatuses, the obtained images are usually displayed in one or more monitors provided in the vicinity of the medical diagnosis apparatuses. This is, for example, for the purpose of checking the obtained images and seeing whether the images are correctly obtained or it is necessary to acquire substitute image at the same position again. Further, the obtained images are sometimes used for the image interpretation immediately right at the place in case of emergency, for example.

FIG. 1 is a diagram showing a configuration of an X-ray diagnosis apparatus with a display according to a prior art. The X-ray diagnosis apparatus shown in FIG. 1 is a so-called bi-plane apparatus which allows obtaining images from two directions at the same time. The X-ray diagnosis apparatus includes a first imaging system comprising a first X-ray tube 1*a*, a first detector 2*a*, and a first holder 3. The X-ray diagnosis apparatus also includes a second imaging system comprising a second X-ray tube 1*b*, a second detector 2*b*, and a second holder 4. Additionally, the apparatus includes a bed table 5, a bed 6, a display 7, a display holder 7*a*, a display panel 8, an operation unit 9, a first rail 10*a*, and a second rail 10*b*.

The first imaging system is for obtaining X-ray images from a first direction. The first X-ray tube 1*a* generates (or radiates) an X-ray which is exposed to a patient to be examined from the first direction. The X-ray exposed to the patient is transmitted through the patient. The detector 2*a* detects the transmitted X-ray. The first holder 3 holds the first X-ray tube 1*a* and the first detector 2*a* by means of an arm connecting the first X-ray tube 1*a* and the first detector 2*a*. The first holder 3 further drives or moves a set of the first X-ray tube 1*a* and the first detector 2*a* in three-dimensional directions.

The second imaging system is for obtaining X-ray images from a second direction. The second X-ray tube 1*b* generates (or radiates) an X-ray which is exposed to the patient to be examined from the second direction. The X-ray exposed to the patient is transmitted through the patient. The detector 2*b* detects the transmitted X-ray. The second holder 4 holds the second X-ray tube 1*b* and the second detector 2*b* by means of an arm connecting the second X-ray tube 1*b* and the second detector 2*b*. The second holder 4 further drives or moves a set of the second X-ray tube 1*b* and the second detector 2*b* in three-dimensional directions.

The patient lies on the bed table 5. The bed 6 has a driving unit which drives and moves the bed table 5 vertically or horizontally. The display 7 comprises a plurality of monitors. In FIG. 1, the display 7 has four monitors. There are two monitors in the horizontal direction and also two monitors ill the vertical direction. Each monitor can be used to display X-ray images obtained in the X-ray diagnosis apparatus. The display 7 is held by the display holder 7*a*. The display panel 8 displays several information related to imaging conditions of the X-ray diagnosis apparatus.

The operation unit 9 is used for determining a position of the bed table 5 by providing designation signals to operate the bed 6. The first rail 10*a* is used for running the second holder 4. The second rail 10*b* is used for running the display holder 7*a*.

Conventional monitors used for the display 7 are known to include CRT (cathode ray tube) monitors. Therefore, they occupy a wide space in the vicinity of the X-ray diagnosis apparatus. The display 7 can be moved along the second rail 10*b*. However, an examination room where the X-ray diagnosis apparatus is usually placed is not so spacious to move away the display 7. Keeping the display 7 around the bed table 5 limits an area where a radiological technologist moves around the patient. Further, it was also a big annoyance to a doctor when the doctor must examine the patient with, for example, a catheter.

Under such a circumstance, an image display monitor is being improved and newly developed with a LCD (crystal liquid display). An LCD monitor is much thinner and lighter than the CRT display monitor. Accordingly, the conventional CRT display monitors are challenged to be replaced with the LCD monitors. Such replacement can be very helpful to apply to the above-explained case. The replacement may be a solution to the prior art problem and may allow giving the radiological technologist and the doctor much more space.

As shown in FIG. 1, however, the display 7 has four monitors. Even if they are replaced with LCD monitors, it is a fact that this number of monitors still occupies a certain space. In practice, these monitors are moved around the bed table 5 in accordance with the manipulation of the doctor, for example. The doctor usually checks an ongoing manipulation status in the monitors. As he changes his position around the bed table 5 (i.e. around the patient) in accordance with his manipulation, the display 7 (or the monitors) must be changed its position so as to allow the doctor to observe images displayed in the display 7.

Such position changes are sometimes performed across and over the patient. The doctor or his aids must be very careful about moving the display 7 over the patient, but, as a matter of fact, it was not easy to do so due to a size of the display comprising four monitors. Particularly, when there are a plurality of monitors in the vertical direction, it is obviously more difficult. The plurality of monitors in the vertical direction may also be a problem when a person, such as the radiological technologist, the doctor, and the aides, are tall enough to bump his or her head against the display. It disturbs their concentration on their work.

BRIEF SUMMARY OF THE INVENTION

According to a first aspect of the present invention, there is provided a medical image diagnosis apparatus, which comprises an image generator configured to generate a medical image, a display, comprising a plurality of monitors, configured to display the medical image, and a mechanism configured to change an arrangement of the plurality of monitors with respect to each of the monitors.

According to a second aspect of the present invention, there is provided a display apparatus for a use in a medical image diagnosis apparatus that generates a medical image. The apparatus comprises a plurality of monitors configured to display the medical image, and a mechanism configured to change an arrangement of the plurality of monitors with respect to each of the monitors.

According to a third aspect of the present invention, there is provided a method of arranging a plurality of monitors which display a medical image in a medical image diagnosis apparatus. The method comprises steps of detecting an operation mode of the medical image diagnosis apparatus, and automatically placing at least one of the plurality of monitors, which is not used in the operation mode detected in the detecting step, behind at least one other of the monitors.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DETAILED DESCRIPTION OF THE PREFERRED EMBODIMENTS

Embodiments of the present invention will be described with reference to the accompanying drawings. The following embodiments of the present invention will be explained with an X-ray diagnosis apparatus as an example of a medical image diagnosis apparatus.

Figure 1:
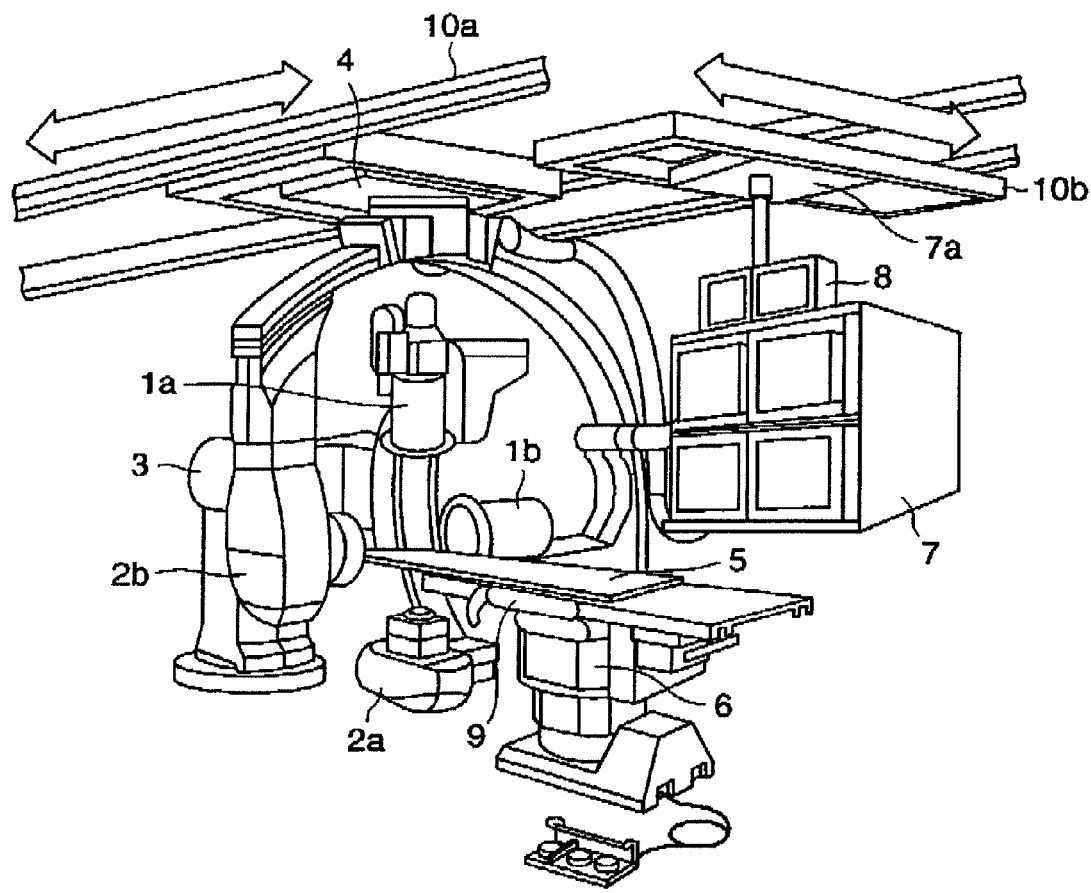
FIG. 1 is a diagram showing a configuration of an X-ray apparatus with a display according to the prior art.
Figure 2:
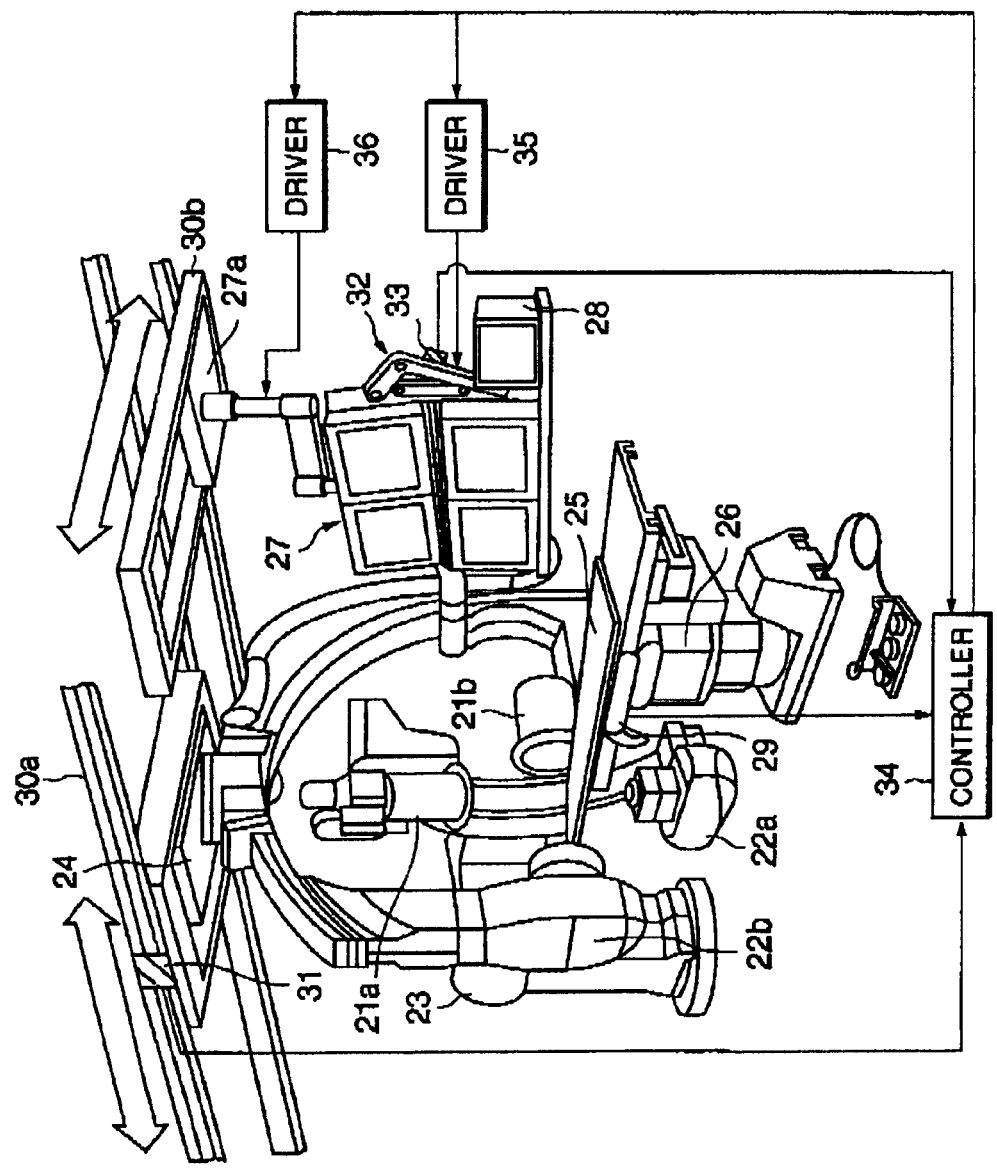
FIG. 2 is a diagram showing a configuration of an X-ray diagnosis apparatus with a display in a bi-plane mode according to an embodiment of the present invention.

FIG. 2 is a diagram showing a configuration of an X-ray diagnosis apparatus with a display according to an embodiment of the present invention. The X-ray diagnosis apparatus shown in FIG. 2 is a so-called bi-plane apparatus which allows obtaining images from two directions at the same time. The X-ray diagnosis apparatus includes a first imaging system comprising a first X-ray tube 21a, a first detector 22a, and a first holder 23. The X-ray diagnosis apparatus also includes a second imaging system comprising a second X-ray tube 21b, a second detector 22b, and a second holder 24. The X-ray diagnosis apparatus further includes a bed table 25, a bed 26, a display 27, a display holder 27a, a display panel 28, an operation unit 29, a first rail 30a, a second rail 30b, a rail sensor 31, a monitor link mechanism 32, a position sensor 33, a controller 34, a link mechanism driver 35, and a display supporter driver 36.

The first imaging system is for obtaining X-ray images from a first direction, such as, for example, a direction from the front to the back of the patient. The first X-ray tube 21a generates (or radiates) an X-ray which is exposed to the patient to be examined from the first direction. The X-ray exposed to the patient is transmitted through the patient. The detector 22a detects the transmitted X-ray. The first holder 23 is fixed on the floor and holds the first X-ray tube 21a and the first detector 22a by means of an arm connecting the first X-ray tube 21a and the first detector 22a. The first holder 23 further drives or moves a set of the first X-ray tube 21a and the first detector 22a in three-dimensional directions.

The second imaging system is for obtaining X-ray images from a second direction, such as, for example, a direction from the right to the left of the patient. The second X-ray tube 21b generates (or radiates) an X-ray which is exposed to the patient to be examined from the second direction. The X-ray exposed to the patient is transmitted through the patient. The detector 22b detects the transmitted X-ray. The second holder 24 is hung from the ceiling and moves along the first rail 30a. The second holder 24 holds the second X-ray tube 21b and the second detector 22b by means of an arm connecting the second X-ray tube 21b and the second detector 22b. Further, the second holder 24 also drives or moves a set of the second X-ray tube 21b and the second detector 22b in three-dimensional directions. The movement of the second holder 24 along the first rail 30a may be sensed by the rail sensor 31, such as a microswitch, at a predetermined position of the first rail 30a so that it can be determined whether the second imaging system is in a position for its use.

The patient lies on the bed table 25. The bed 26 has a driving unit which drives and moves the bed table 25 vertically or horizontally. The display 27 comprises a plurality of monitors.

In FIG. 2, the display 27 has four monitors. Each of the monitors may be an LCD monitor. There are two monitors in the horizontal direction and also two monitors in the vertical direction. For example, two of the monitors may be used for the first imaging system. One of the two monitors may be used for displaying an original image obtained in the first imaging system, and the other one may be used for displaying a processed image resulting from processing the original image or others. These two monitors may be laid in a lower stand of the display 27. Another two of the monitors may be used for the second imaging system. One of these monitors may be used for displaying an original image obtained in the second imaging system, and the other one may be used for displaying a processed image resulting from processing the original image or others. These other two monitors may be laid in a upper stand of the display 27.

The two monitors in the lower stand and the two monitors in the upper stand may be linked to each other by the monitor link mechanism 32. The link mechanism driver 35 drives the monitor link mechanism 32 so as to move the position of the monitors relative to each other. The position sensor 33 may sense a status of the monitor link mechanism 32. The details of the link mechanism driver 35 and the position sensor 33 will be explained later. The display 27 is held in a rotatable manner by the display holder 27a and so hung from the ceiling. The display holder 27a moves along the second rail 30b. The display 27 is also changed its height from the floor by the display supporter driver 36. The display supporter driver 36 may control to adjust the height of the display 27 to a height appropriate for the doctor or the like to observe images displayed in the display 27.

The display panel 28 displays several information related to imaging conditions of the X-ray diagnosis apparatus, such as positions of the first holder 23, the second holder 24, and the bed table 25 and X-ray quantities radiating from the first X-ray tube 21a and from the second X-ray tube 21b.

The operation unit 29 is used for determining a position of the bed table 25 by providing designation signals to operate the bed 26. Further, the operation unit 29 may also be used for adjusting a position of the first holder 23, a position of the second holder 24, a position of the set of the first X-ray tube 21a and the first detector 22a, and a position of the set of the second X-ray tube 21b and the second detector 22b.

The controller 34 controls each component or unit of the X-ray diagnosis apparatus, which has been described above.

The X-ray diagnosis apparatus with a bi-plane feature may usually be used for, for example, an X-ray fluoroscopy with a contrast agent in an examination of a left ventriculography or a cardiac examination for an infant. Since the bi-plane examination makes it possible to obtain images from two different directions at the same time, it can reduce an amount of the enhancement agent to be used for a patient.

When the X-ray diagnosis apparatus is operated in a bi-plane mode, two monitors in a lower stand may be used to display images obtained in the first imaging system and two monitors in an upper stand may be used to display images obtained in the second imaging system, as mentioned above. When, however, the X-ray diagnosis apparatus is used in a single-plane mode, that is to say, when, for example, only the first imaging system is used to obtain images, it may not be necessary to use all the four monitors in the display 27.

Figure 3:
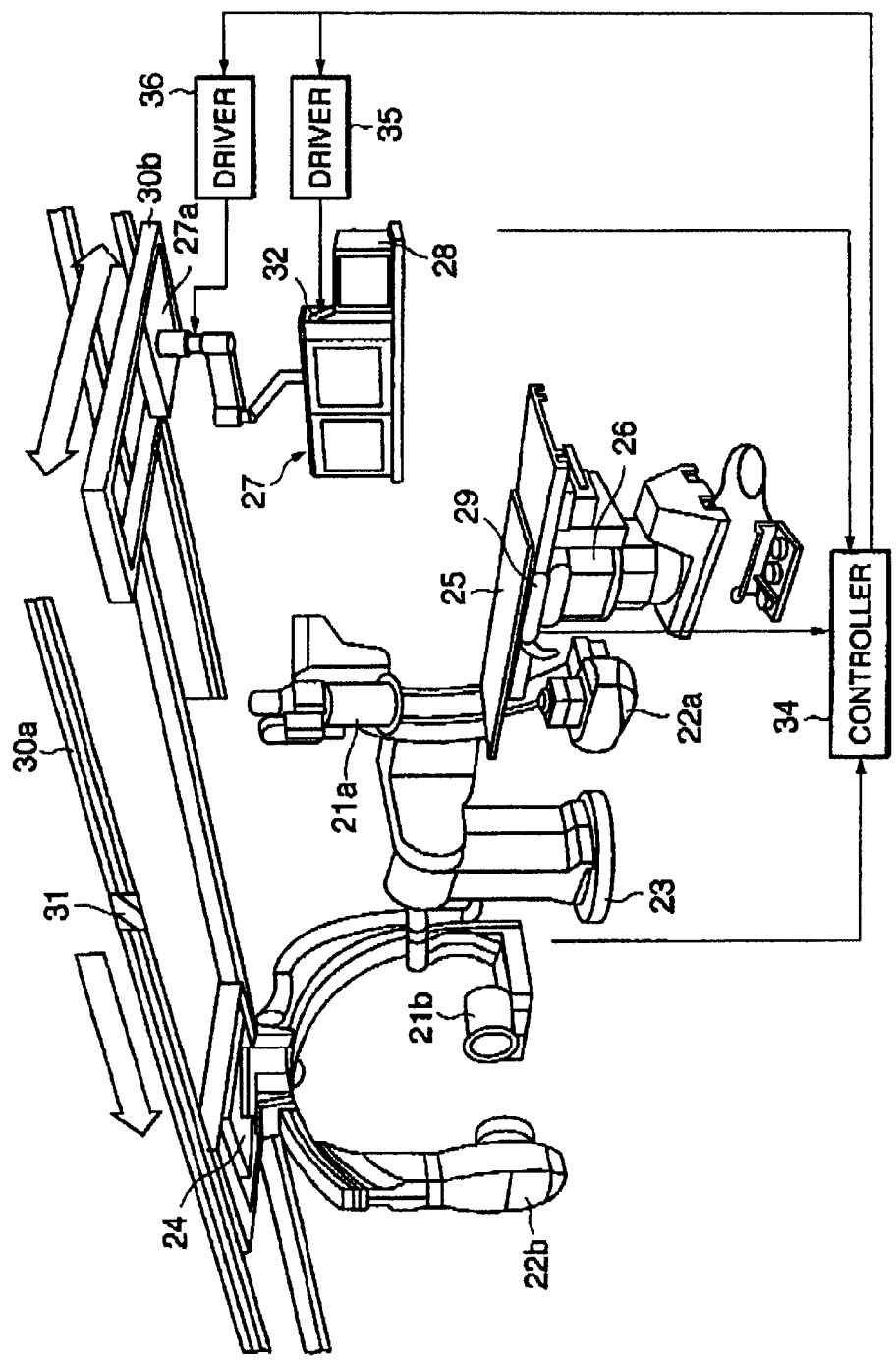
FIG. 3 is a diagram showing another configuration of an X-ray diagnosis apparatus with a display in a single-plane mode according to an embodiment of the present invention.

FIG. 3 is a diagram showing another configuration of an X-ray diagnosis apparatus with a display in the single-plane mode according to an embodiment of the present invention. As shown in FIG. 3, the second imaging system comprising the second X-ray tube 21b, the second detector 22b, and the second holder 24 may be slid back away from the bed table 25 when the X-ray diagnosis apparatus is operated in the single-plane mode. This makes it easier to perform an examination since it provides more space around the bed table 25. The doctor and the radiological technologist are given more space to move around the bed table 25. Further, the display 27 is made compact since an examination in the single-plane mode does not require all the four monitors to display images. Here is an example that only two monitors are required in the single-plane mode. In the display 27, monitors in the upper stand have been moved behind the monitors in the lower stand. This can be accomplished by sliding one monitor behind or in front of another monitor. Likewise, such a re-arrangement can be accomplished by folding one monitor behind or in front of another monitor. In such a circumstance, the doctor or the radiological technologist is given still further more space to move around the bed table 25. This example of the display 27 will be explained with reference to FIGS. 4 and 5.

Figure 4:
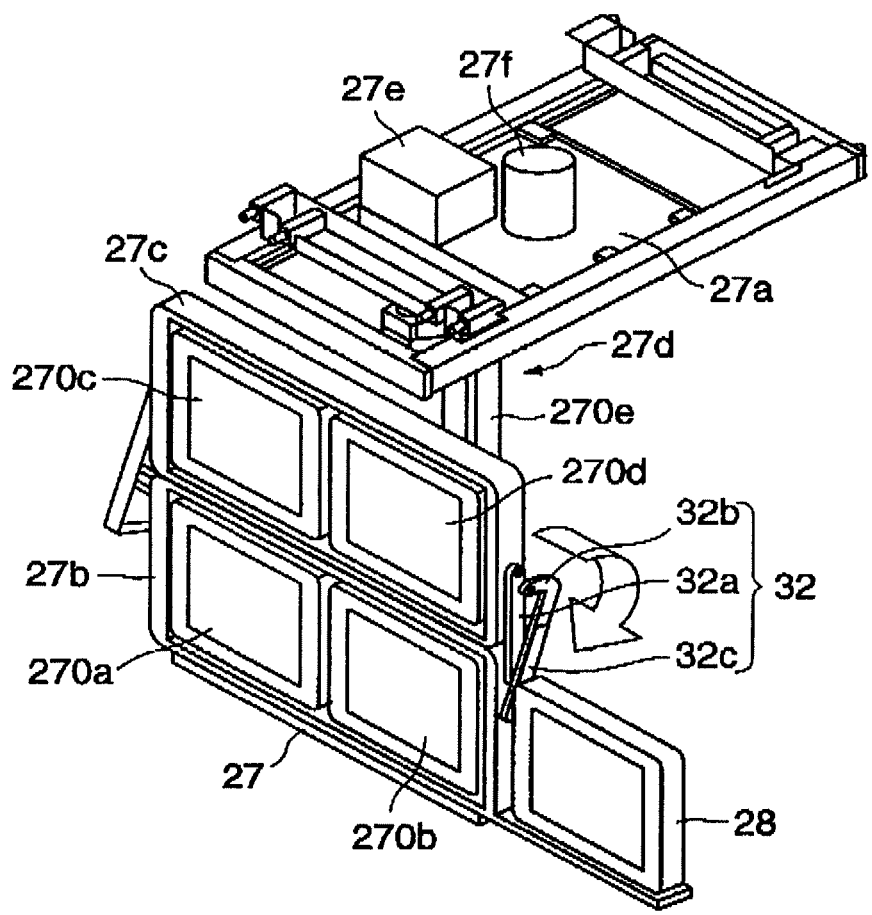
FIG. 4 is a diagram showing a configuration of a display according to an embodiment of the present invention.

FIG. 4 is a diagram showing a configuration of the display 27 according to an embodiment of the present invention. The display 27 is connected to the display holder 27a via a supporter 27d. The display 27 has a lower monitor frame 27b and an upper monitor frame 27c. The lower monitor frame 27b fixes a first monitor 270a and a second monitor 270b. The display panel 28 may also be fixed in the lower monitor frame 27b. The upper monitor frame 27c fixes a third monitor 270c and a fourth monitor 270d. The monitor link mechanism 32 comprises a straight arm 32a in a form similar to a letter 'I', an L arm 32b in a form similar to a letter 'L', and an arm driver 32c. The arm driver 32c may be, for example, an air cylinder, a hydraulic cylinder, or an electric power cylinder, so as to be controlled its length. An arm driving unit 27e provided in the display holder 27a drives the arm driver 32c. The arm driving unit 27e may be, for example, an air compressor, a hydraulic pump, or a power source, and be connected to the arm driver 32c via an air tube, a hydraulic hose, or a power cord. The arm driving unit 27e may be controlled by the link mechanism driver 35.

Figure 5:
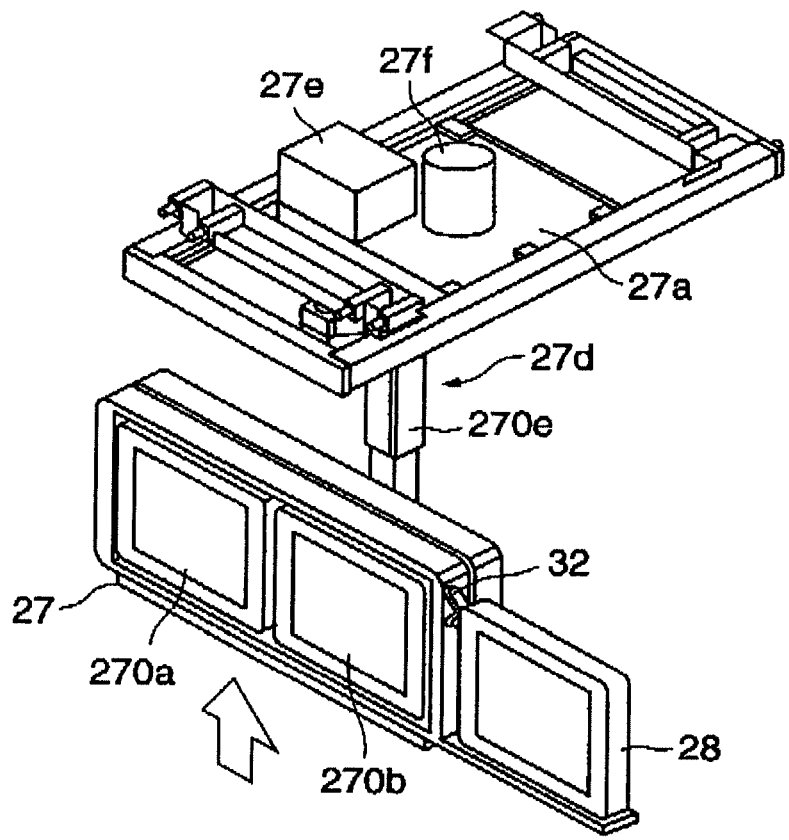
FIG. 5 is a diagram showing another configuration of the display according to an embodiment of the present invention.

As explained above, for example, when the X-ray diagnosis apparatus is operated in the single-plane mode, the second imaging system is slid away from the bed table 25 to the backward. Such movement of the second imaging system is sensed by the rail sensor 31 and is reported to the controller 34. Responsive to the report from the rail sensor 31, the controller 34 controls the link mechanism driver 35 so that the link mechanism driver 35 controls the arm driving unit 27e. The arm driving unit 27e drives the arm driver 32c to change its length. In accordance with the length of the arm driver 32c, the straight arm 32a and the L arm 32b are moved correspondingly. Accordingly, the upper monitor frame 27c is moved and placed behind the lower monitor frame 27b as shown in FIG. 5.

When the upper monitor frame 27c is placed behind the lower monitor frame 27b, the position sensor 33 senses an expanded position or a screw position of the arm driver 32c and reports such a position to the controller 34. In addition, when the upper monitor frame 27c is placed behind the lower monitor frame 27b, the center of the display 27 is changed its position. In this embodiment, the center of the display 27 is vertically lowered to the floor, compared to the position of before the position change.

The supporter 27d includes a supporter driver 270e. As similar to the arm driver 32c, the supporter driver 270e may be, for example, an air cylinder, a hydraulic cylinder, or an electric power cylinder, so as to be controlled its length. The supporter driver 270e is driven by a supporter driving unit 27f provided in the display holder 27a. The supporter driving unit 27f may be, for example, an air compressor, a hydraulic pump, or a servomotor, and be connected to the supporter driver 270e. The supporter driving unit 27f may be controlled by the display supporter driver 36. In the above case, responsive to the report from the position sensor 33 and maybe also from the rail sensor 31, the controller 34 may also control the display supporter driver 36 so that the display supporter driver 36 controls the supporter driving unit 27f The supporter driving unit 27f drives the supporter driver 270e to change its length. Accordingly, the display 27 may be pulled up towards the ceiling and adjust its position to the height appropriate to observe images displayed in the display 27.

On the other hand, when the rail sensor 31 senses the second imaging system coming back towards the bed table 25, the action of the display 27 and its peripherals may obviously be the opposite to the above description. As a result, the upper monitor frame 27c can be lifted up to its original position, and accordingly the display 27 presents four monitors again.

In addition, the change of arranging the monitors of the display 27 is not limited to whether the X-ray diagnosis apparatus is operated in the bi-plane mode or in the single-plane mode. Sensing any other actions, triggers, or manual changes may be applicable as alternative embodiments of the present invention.

Figure 6:
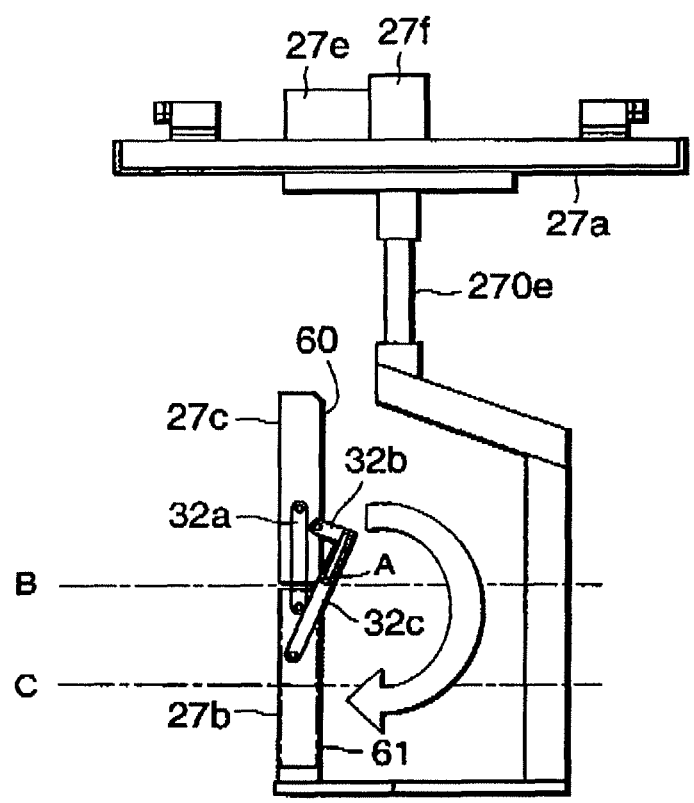
FIG. 6 is a diagram showing a side aspect of the display and its peripherals with monitors placed at an original position according to an embodiment of the present invention.

FIG. 6 is a diagram showing a side aspect of the display 27 and its peripherals with the monitors placed at an original position according to an embodiment of the present invention. As shown in FIG. 6, when the upper monitor frame 27c gets placed behind the lower monitor frame 27b, the upper monitor frame 27c is folded towards the lower monitor frame 27b so that a back 60 of the upper monitor frame 27c is faced with a back 61 of the lower monitor frame 27b. Here, the folding is achieved by rotation of the upper monitor frame 27c around an axis A. Therefore, there is required quite a wide space behind the upper monitor frame 27c and the lower monitor frame 27b so as to allow the upper monitor frame 27c to rotate around the axis A. A preferable height B of the display 27 may be determined to become a border between the upper monitor frame 27c and the lower monitor frame 27b. In other words, the center of the display 27 in the vertical direction may be set to the height B. When the center of the display 27 in the vertical direction is set to the height B, the center of the lower monitor frame 27b in the vertical direction is positioned at the height C.

Figure 7:
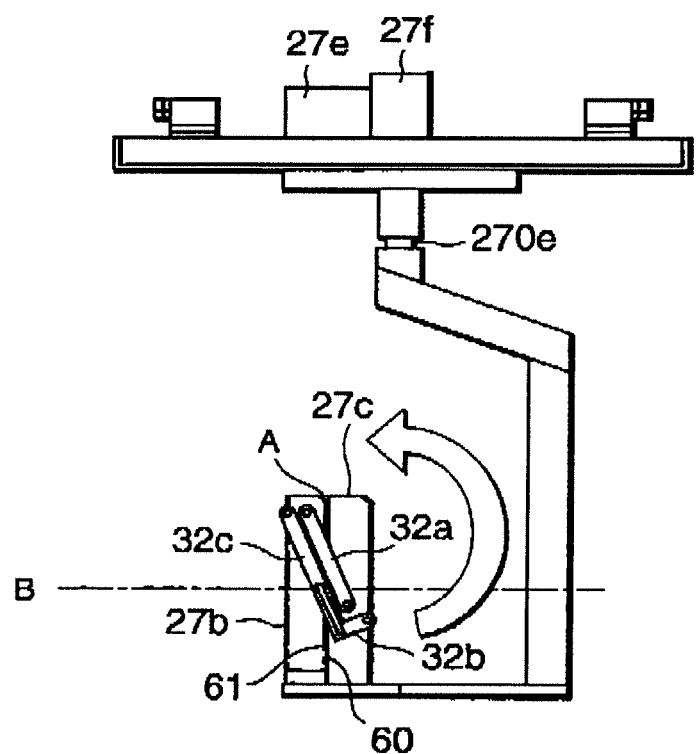
FIG. 7 is a diagram showing a side aspect of the display and its peripherals with the monitors placed at a folded position according to an embodiment of the present.

FIG. 7 is a diagram showing a side aspect of the display 27 and its peripherals with the monitors placed at a folded position according to an embodiment of the present invention. As shown in FIG. 7, when the upper monitor frame 27c is folded to the lower monitor frame 27b, the display 27 is controlled to change its height so that the center of the display 27 in the vertical direction still keeps the height B. Here, the center of the display 27 is identical with the center of the lower monitor frame 27b. Therefore, the display 27 is pulled up a distance (B-C) to keep the preferable height B, by controlling the length of the supporter driver 270e. When the upper monitor frame 27c gets returned to its original position, that is, a position on top of the lower monitor frame 27b, the upper monitor frame 27c is rotated around the axis A again.

Figure 8:
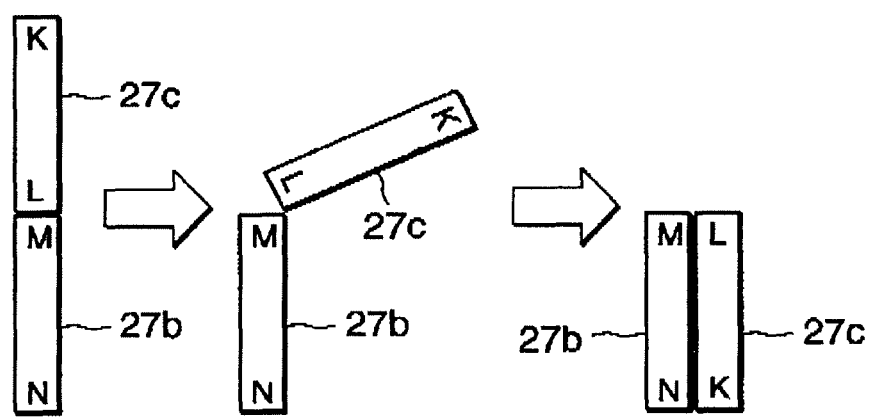
FIG. 8 is a diagram showing side aspects of the display when the upper monitor frame 27c is folded according to an embodiment of the present invention.

The folding aspects of the upper monitor frame 27c described with FIGS. 6 and 7 will be clearer in FIG. 8 FIG. 8 is a diagram showing side aspects of the display 27 when the upper monitor frame 27c is folded according to an embodiment of the present invention. In FIG. 8, to make it easy to understand the folding, the top end of the upper monitor frame 27c is marked 'K' while the bottom end of the upper monitor frame 27c is marked 'L'. Similarly, the top end of the lower monitor frame 27b is marked 'M' while the bottom end of the lower monitor frame 27b is marked 'N'. When the folding has been completed, the top end K of the upper monitor frame 27c faces the bottom end N of the lower monitor frame 27b Further, the bottom end L of the upper monitor frame 27c faces the top end M of the lower monitor frame 27b.

Alternatively, the upper monitor frame 27c of the display 27 may be placed behind the lower monitor frame 27b of the display 27 in the following manners.

Figure 9:
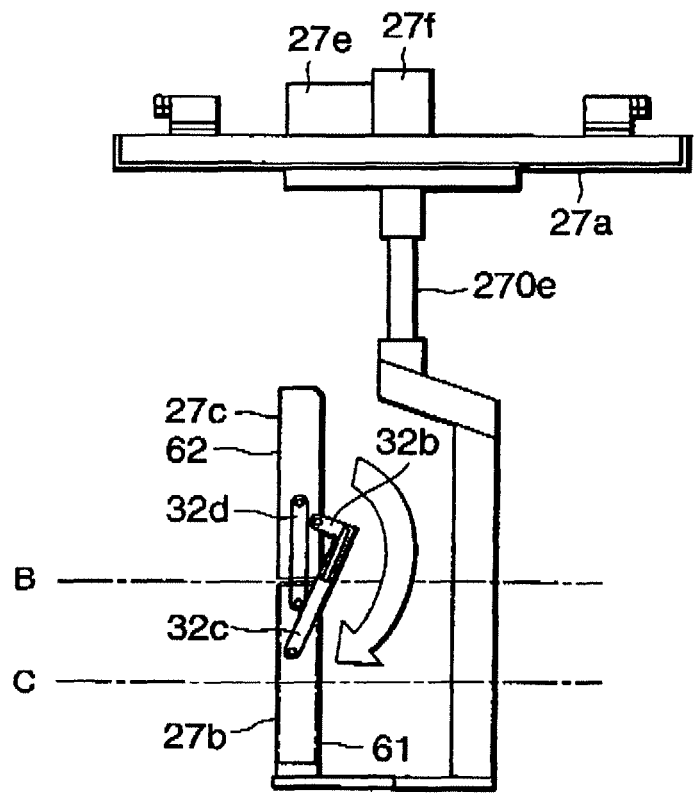
FIG. 9 a diagram showing another side aspect of the display and its peripherals with the monitors placed at an original position according to an embodiment of the present invention.

FIG. 9 is a diagram showing another side aspect of the display 27 and its peripherals with the monitors placed at an original position according to an embodiment of the present invention. In FIG. 9, there is a variable arm 32d in connection with the L arm 32b and the arm driver 32c, instead of the straight arm 32a The variable arm 32d varies its length flexibly. When the upper monitor frame 27c gets placed behind the lower monitor frame 27b, the upper monitor frame 27c slides to the backside of the lower monitor frame 27b so that a front 62 of the upper monitor frame 27c is faced with the back 61 of the lower monitor frame 27b. Since the upper monitor frame 27c slides quite linearly, there is required only a narrow space behind the upper monitor frame 27c and the lower monitor frame 27b so that the display 27 and its peripherals can become more compact and so allow the doctor and the radiological technologist a more space around the bed table 25. The preferable height B of the display 27 may be determined to become a border between the upper monitor frame 27c and the lower monitor frame 27b. As similar to FIG. 6, the center of the display 27 in the vertical direction may be set to the height B. When the center of the display 27 in the vertical direction is set to the height B, the center of the lower monitor frame 27b in the vertical direction is positioned at the height C.

Figure 10:
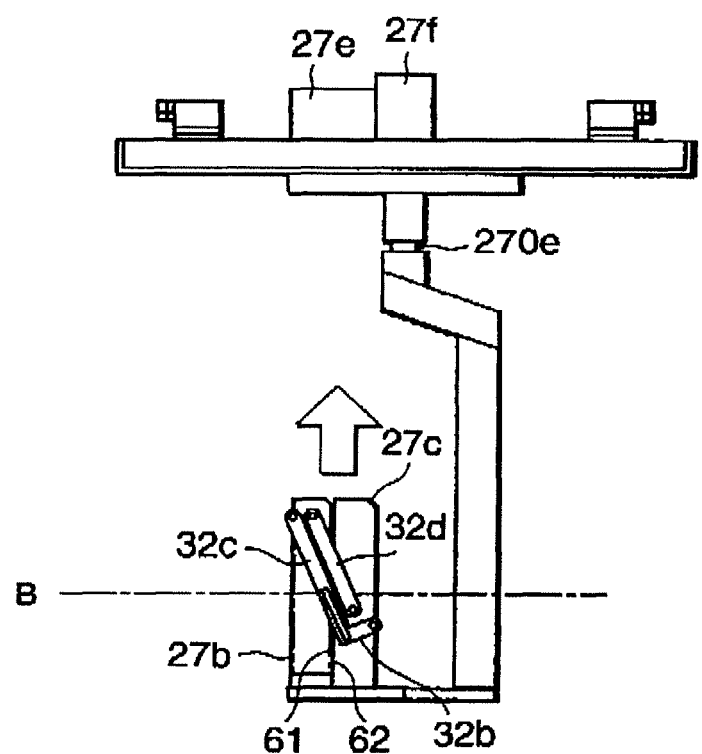
FIG. 10 is a diagram showing a side aspect of the display 27 and its peripherals with the monitors placed at a slid position according to an embodiment of the present invention.

FIG. 10 is a diagram showing a side aspect of the display 27 and its peripherals with the monitors placed at a slid position according to an embodiment of the present invention. As shown in FIG. 10, when the upper monitor frame 27c slides to the backside of the lower monitor frame 27b, the display 27 is controlled to change its height so that the center of the display 27 in the vertical direction still keeps the height B. Here the center of the display 27 is identical with the center of the lower monitor frame 27b. Therefore, as similar to FIG. 7, the display 27 is pulled up a distance (B-C) to keep the preferable height B, by controlling the length of the supporter driver 270e. When the upper monitor frame 27c gets returned to its original position, that is, a position on top of the lower monitor frame 27b, the upper monitor frame 27c slides back upwards.

Figure 11:
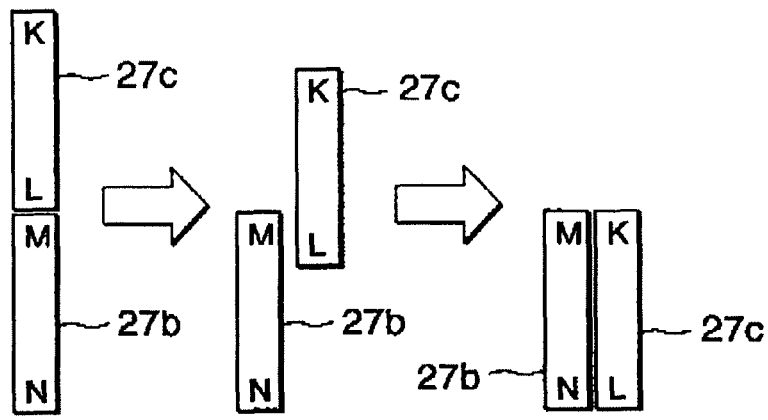
FIG. 11 is a diagram showing side aspects of the display 27 when the upper monitor frame 27c slides according to an embodiment of the present invention.

The sliding aspects of the upper monitor frame 27c described with FIGS. 9 and 10 will be clearer in FIG. 11. FIG. 11 is a diagram showing side aspects of the display 27 when the upper monitor frame 27c slides according to an embodiment of the present invention. In FIG. 11, to make it easy to understand the sliding, each end of the upper monitor frame 27c and the lower monitor frame 27b is marked the same reference as in FIG. 8. When the sliding has been completed, the top end K of the upper monitor frame 27c faces the top end M of the lower monitor frame 27b. Further, the bottom end L of the upper monitor frame 27c faces the bottom end N of the lower monitor frame 27b.

Figure 12:
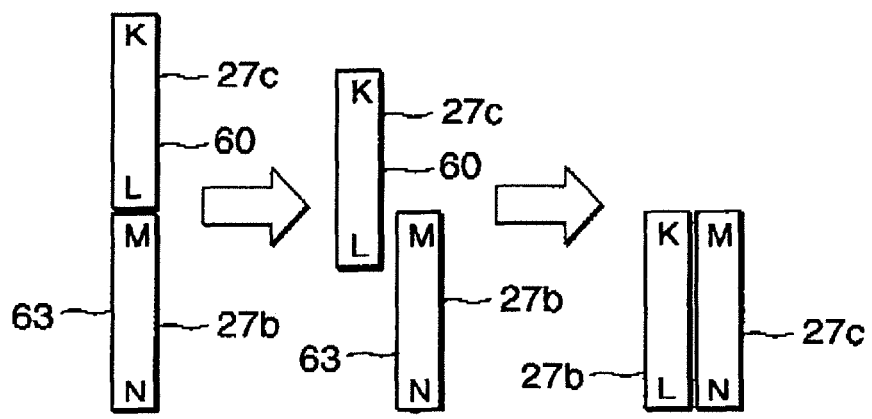
FIG. 12 is a diagram showing an alternative example of the sliding according to an embodiment of the present invention.

FIG. 12 shows an alternative example of the sliding described in FIGS. 9 to 11 and is a diagram showing another side aspect of the display 27 when the upper monitor frame 27c slides according to the embodiment of the present invention. The alternative example shown in FIG. 12 is a case that the upper monitor frame 27c may slide to the front of the lower monitor frame 27b so that the back 60 of the upper monitor frame 27c is faced with a front 63 of the lower monitor frame 27b. To make it easy to understand the sliding, each end of the upper monitor frame 27c and the lower monitor frame 27b is marked the same reference as in FIG. 11. When the sliding has been completed, the top end K of the upper monitor frame 27c faces the top end M of the lower monitor frame 27b. Further, the bottom end L of the upper monitor frame 27c faces the bottom end N of the lower monitor frame 27b.

According to embodiments of the present invention, the display arrangement can be performed in various ways. In the above description, holding and sliding techniques have been described in terms of viewing the display 27 from its side aspect. Embodiments of the present invention may not be limited to those described above. Further examples of the display arrangement will be described with reference to FIGS. 13 to 20. FIGS. 13 to 20 show various arrangement forms of the monitors. However, these are only exemplary forms and embodiments of the present invention are not limited to these. Each of the arrangement forms may utilize one or more of the folding and/or the sliding techniques described above.

Figure 13:
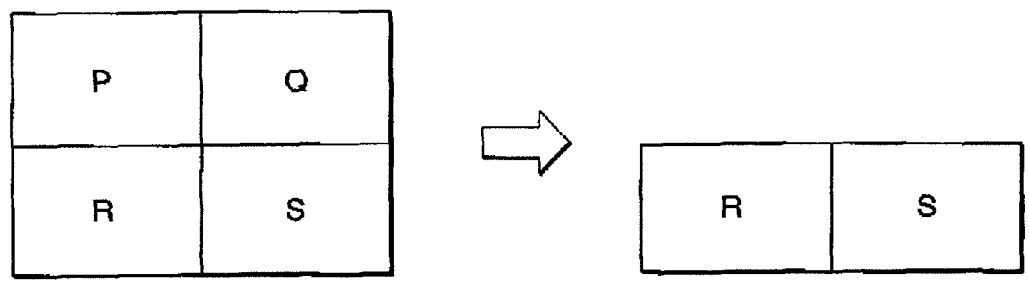
FIG. 13 is a diagram showing a first arrangement viewed from a front aspect of a display according to an embodiment of the present invention.

FIG. 13 is a diagram showing a first arrangement viewed from a front aspect of a display according to an embodiment of the present invention.

As shown in FIG. 13, the display may comprise four monitors P, Q, R, and S. The monitors P and Q may be placed behind the monitors R and S as described in FIG. 8 or 11. Similarly, the monitors R and S may be placed in front of the monitors P and Q. In a third way, the monitor P may be placed behind the monitor Q and the monitors P and Q may be placed behind the monitor S by sliding. In a fourth way, the monitor P may be placed in front of the monitor Q and the monitors P and Q may be placed behind the monitor S by folding. In similar manner, there are more possible ways for achieving this arrangement. Accordingly, the monitors R and S are used to display images.

Figure 14:
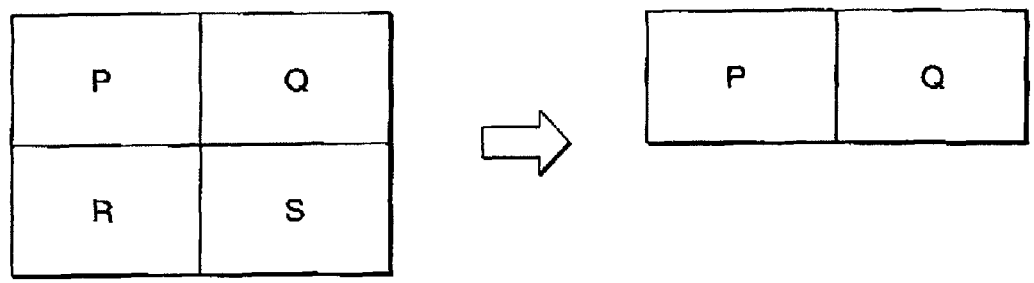
FIG. 14 is a diagram showing a second arrangement viewed from the front aspect of the display according to an embodiment of the present invention.

FIG. 14 is a diagram showing a second arrangement viewed from the front aspect of the display according to an embodiment of the present invention.

As shown in FIG. 14, the display may comprise four monitors P, Q, R, and S. The monitors R and S may be placed behind the monitors P and Q. Similarly, the monitors P and Q may be placed in front of the monitors R and S as described in FIG. 12. In a third way, the monitor S may be placed behind the monitor R and the monitors R and S may be placed behind the monitor P by sliding. In a fourth way, the monitor S may be placed in front of the monitor R and the monitors R and S may be placed behind the monitor P by folding. In similar manner, there are more possible ways for achieving this arrangement. Accordingly, the monitors P and Q are used to display images.

Figure 15:
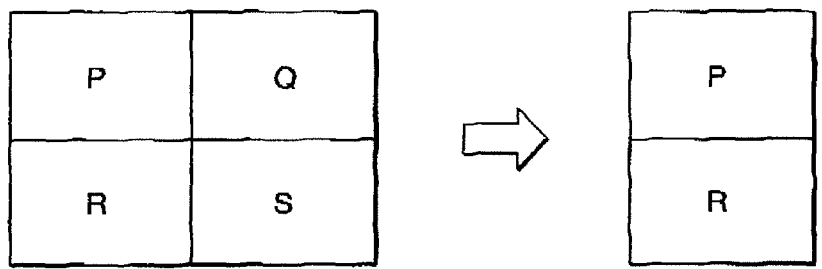
FIG. 15 is a diagram showing a third arrangement viewed from the front aspect of the display according to an embodiment of an present invention.

FIG. 15 is a diagram showing a third arrangement viewed from the front aspect of the display according to an embodiment of the present invention.

As shown in FIG. 15, the display may comprise four monitors P, Q, R, and S. The monitors Q and S may be placed behind the monitors P and R. Alternatively, the monitors P and R may be placed in front of the monitors Q and S. Further, the monitor Q may be placed behind the monitor S and the monitors Q and S may be placed behind the monitor R by sliding. Further still, the monitor Q may be placed in front of the monitor S and the monitors Q and S may be placed behind the monitor R by folding. In similar manner, there are more ways for achieving this arrangement. Accordingly, the monitors P and R are used to display images.

Figure 16:
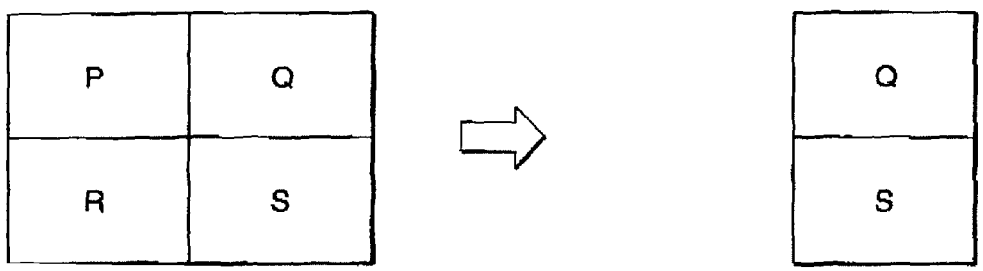
FIG. 16 is a diagram showing a fourth arrangement viewed from the front aspect of the display according to an embodiment of the present invention.

FIG. 16 is a diagram showing a fourth arrangement viewed from the front aspect of the display according to an embodiment of the present invention.

As shown in FIG. 16, the display may comprise four monitors P, Q, R, and S. The monitors P and R may be placed behind the monitors Q and S. Alternatively, the monitors Q and S may be placed in front of the monitors P and R. Further, the monitor R may be placed behind the monitor P and the monitors P and R may be placed behind the monitor Q by sliding. Further still, the monitor R may be placed in front of the monitor P and the monitors P and R may be placed behind the monitor Q by folding. In similar manner, there are more ways for achieving this arrangement. Accordingly, the monitors Q and S are used to display images.

Figure 17:
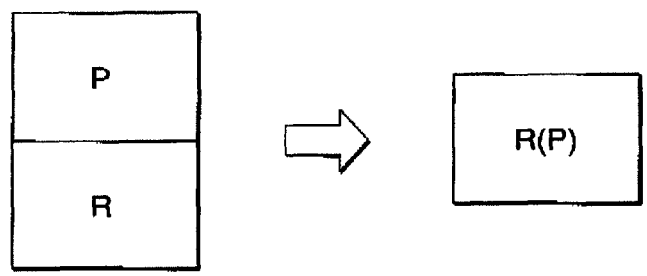
FIG. 17 is a diagram showing a fifth arrangement viewed from the front aspect of the display according to an embodiment of the present invention.

FIG. 17 is a diagram showing a fifth arrangement viewed from the front aspect of the display according to an embodiment of the present invention.

As shown in FIG. 17, the display may comprise two monitors P and R. The monitor P may be placed behind the monitor R. It is another way that the monitor R may be placed in front of the monitor P. Accordingly, the monitor R is used to display images. Alternatively, the monitor R may be placed behind the monitor P. It is another way that the monitor P may be placed in front of the monitor R. Accordingly, the monitor P is used to display images.

Figure 18:
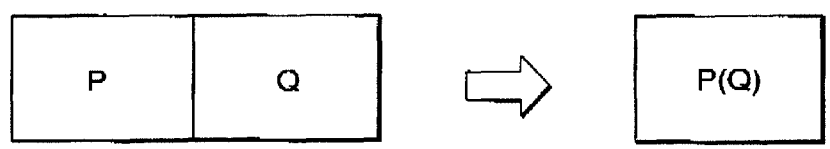
FIG. 18 is a diagram showing a sixth arrangement viewed from the front aspect of the display according to an embodiment of the present invention.

FIG. 18 is a diagram showing a sixth arrangement viewed from the front aspect of the display according to an embodiment of the present invention.

As shown in FIG. 18, the display may comprise two monitors P and Q. The monitor Q may be placed behind the monitor P. It is another way that the monitor P may be placed in front of the monitor Q. Accordingly, the monitor P is used to display images. Alternatively, the monitor P may be placed behind the monitor Q. It is another way that the monitor Q may be placed in front of the monitor P. Accordingly, the monitor Q is used to display images.

Figure 19:
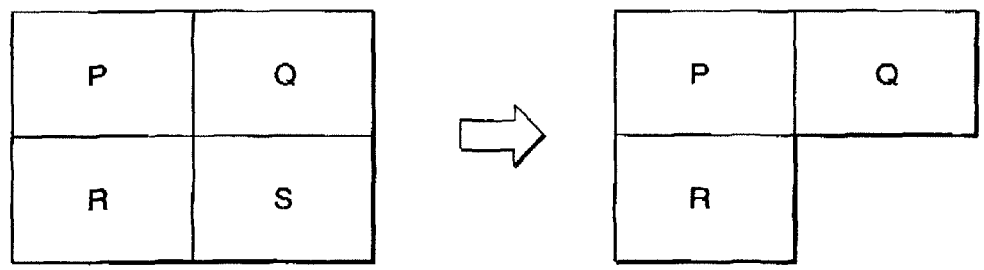
FIG. 19 is a diagram showing a seventh arrangement viewed from the front aspect of the display according to an embodiment of the present invention.

FIG. 19 is a diagram showing a seventh arrangement viewed from the front aspect of the display according to an embodiment of the present invention.

As shown in FIG. 19, the display may comprise four monitors P. Q. R, and S. The monitor S may be placed behind the monitor Q. It is another way that the monitor S may be placed behind the monitor R. Accordingly, the monitors P, Q, and R are used to display images.

Figure 20:
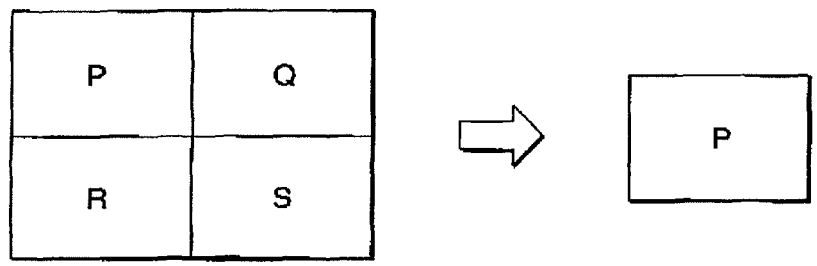
FIG. 20 is a diagram showing a eighth arrangement viewed from the front aspect of the display according to an embodiment of the present invention.

FIG. 20 is a diagram showing a eighth arrangement viewed from the front aspect of the display according to an embodiment of the present invention.

As shown in FIG. 20, the display may comprise four monitors P, Q, R, and S. It is the first way that the monitors Q and S may be placed behind the monitors P and R and the monitors R and S may be placed behind the monitors P and Q. It is the second way that the monitors R and S may be placed behind the monitors P and Q and the monitors Q and S may be placed behind the monitors P and R. It is the third way that the monitor S may be placed behind the monitors Q and the monitors Q and S may be placed behind the monitor P, and in addition, the monitor R may be placed behind the monitors P, Q, and S. In similar manner, there are more ways for achieving this arrangement. Accordingly, the monitor P is used to display images.

The arrangement of monitors of the display can be changed in various manners as described above. When the X-ray diagnosis apparatus is operated in the single-plane mode, it may not be necessary to move the second imaging system towards the back. Whether the second imaging system is moved or not, it may not be necessary that the display arrangement always automatically corresponds to the mode of whether bi-plane or single-plane.

Figure 21:
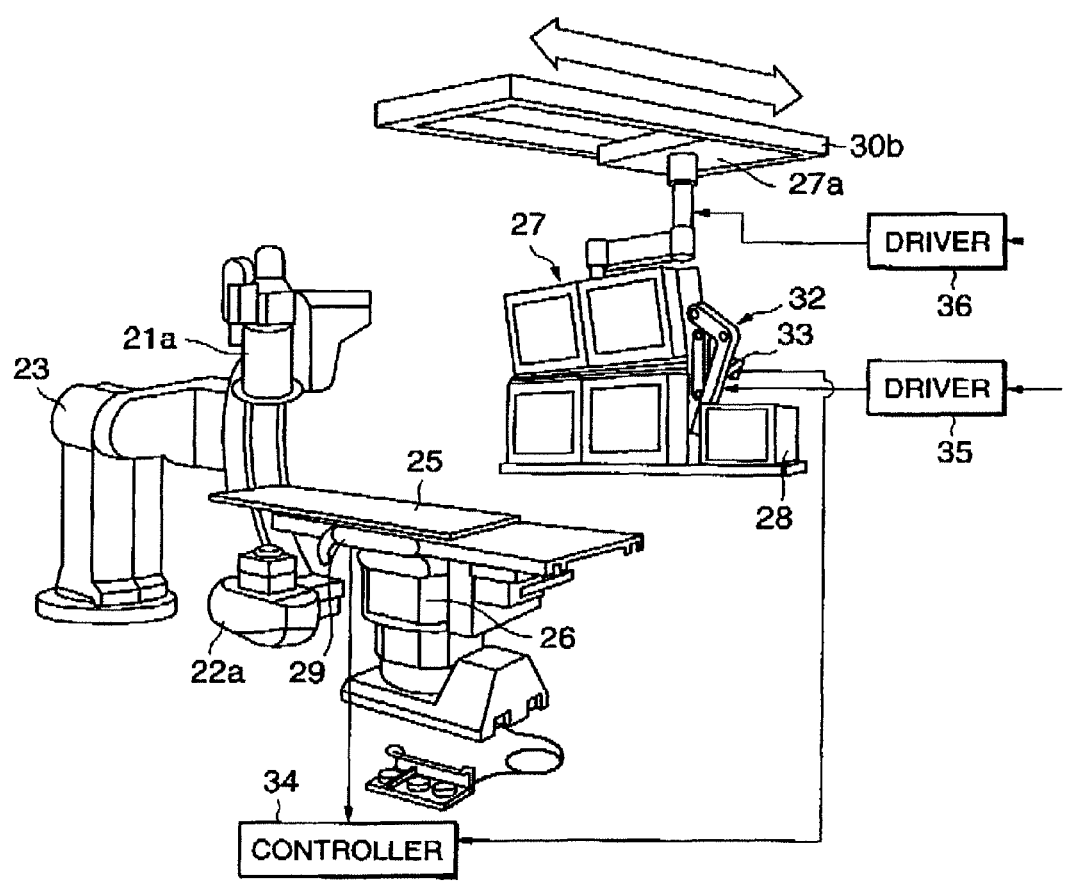
FIG. 21 is a diagram showing still another configuration of an X-ray diagnosis apparatus with a display according to an embodiment of the present invention.

Further, the X-ray diagnosis apparatus according to embodiments of the present invention is not limited to the bi-plane apparatus, but may also be applied to an ordinary X-ray diagnosis apparatus with only one imaging system as shown in FIG. 21.

Still further, the principles of the present invention may also be applied to other medical diagnosis apparatuses, such as, for example, an X-ray CT apparatus, an MRI apparatus, a nuclear medical diagnosis apparatus, an ultrasound diagnosis apparatus, and an endoscopic image apparatus.

For manual operations, by the doctor, the radiological technologist, or the like, of the display arrangement and/or the height of the display 27, it may be possible to provide the operation unit 29 with one or more buttons or switches for an exclusive use in such manual operations. According to input operations with the buttons or switches in the operation unit 29, the input information may be sent to the controller 34. The controller 34 controls the link mechanism driver 35 and the display supporter driver 36. The link mechanism driver 35 controls the arm driving unit 27e which drives the arm driver 32c so as to change the arrangement of the monitors. The display supporter driver 36 controls the supporter driving unit 27f which drives the supporter driver 270e so as to change the height of the display 27.

Alternatively, if the arrangement of monitors and/or the height of the display 27 are changed in manual without any electrical input operations, it may be achieved by reducing or removing load or holding power of the arm driver 32c and/or the supporter driver 270e so as to allow the doctor or the like to make the arrangement of the display by himself. However, the weight of the display 27 or monitors may be a problem for such direct manual operations. Therefore, it may be necessary to prepare a fixer, such as fixing screws, to fix the display 27 or monitors to the supporter 27d or the monitor link mechanism 32 at a desired position. Further, it may also be necessary to prepare a helper, such as gas springs, in the monitor link mechanism 32 for the purpose of helping manual operations of the doctor or the like.

Still furthermore, the mechanism of how to connect the monitors of the display is not limited to those disclosed in the embodiment of the present invention, but can apply any other mechanism including various well-known mechanism thereto.

According to embodiments of the present invention, the arrangement of a plurality of monitors of a display can advantageously be changed. In the arrangement of the monitors, the number of the monitors to be spread out can be reduced by superposing a part of the monitors on the rest of the monitors. Therefore, it may make it possible to reduce a space occupied by the display around the bed table (or a patient) so that a doctor, a radiological technologist, or the like can concentrate on his or her work. This results in improving a quality of his or her manipulation.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the alcove disclosure in the embodiments of the present invention is obtained.

What is claimed is:

1. A medical image diagnosis apparatus, comprising:
   at least one medical X-ray imaging device configured to perform medical X-ray imaging and to generate a medical image;
   a display, comprising a plurality of monitors, configured to display the medical image; and
   a mechanism configured to change, based on movement of one of the at least one medical X-ray imaging device away from a patient bed to a predetermined position, as detected by at least one sensor of the medical image diagnosis apparatus, a physical arrangement of the plurality of monitors with respect to each of the monitors so that a first monitor is positioned to superpose a second monitor, thereby rendering the second monitor at least partially unviewable from any viewing angle.

2. The apparatus according to claim 1, wherein the plurality of monitors are arranged adjacent to one another.

3. The apparatus according to claim 1, wherein the mechanism is configured to slide at least one of the plurality of monitors behind at least one other of the plurality of monitors.

4. The apparatus according to claim 1, wherein the mechanism is configured to fold at least one of the plurality of monitors behind at least one other of the plurality of monitors.

5. The apparatus according to claim 1, wherein the mechanism is configured to slide at least one of the plurality of monitors in front of at least one other of the plurality of monitors.

6. The apparatus according to claim 1, wherein the mechanism is configured to fold at least one of the plurality of monitors in front of at least one other of the plurality of monitors.

7. The apparatus according to claim 1, wherein the at least one medical X-ray imaging device comprises a plurality of medical X-ray imaging devices, each comprising a generation device and a detection device detecting a generated part of the medical image and wherein the mechanism is configured to change the physical arrangement based on how many of the plurality of medical X-ray imaging devices are used.

8. The apparatus according to claim 7, wherein the mechanism is configured to change the physical arrangement based on a required number of monitors in each of the plurality of medical X-ray imaging devices to be used.

9. The apparatus according to claim 7, wherein at least one unused monitor of the plurality of monitors, which is not being used by the plurality of medical X-ray imaging devices, is changed its placement relative to the physical arrangement.

10. The apparatus according to claim 9, wherein the at least one unused monitor is behind at least one other of the monitors.

11. The apparatus according to claim 10, wherein the other monitor is at least one of the plurality of monitors, which is used in a use of one or more of the plurality of medical X-ray imaging devices.

12. The apparatus according to claim 6, wherein the at least one medical X-ray imaging device comprises a single medical X-ray imaging device which further comprises a generation device and a detection device detecting a generated part of the medical image, and wherein the mechanism is configured to change the physical arrangement of the plurality of monitors based on a use of the apparatus with the single medical X-ray imaging device.

13. The apparatus according to claim 1, further comprising a position controller configured to adjust a center of the display to be constant at least either vertically or horizontally, regardless of the arrangement.

14. A display apparatus for a use in a medical image diagnosis apparatus that generates a medical image, comprising:
 a plurality of monitors configured to display the medical image, and
 a mechanism configured to change, based on movement of one of a plurality of medical X-ray imaging devices away from a patient bed to a predetermined position, as detected by at least one sensor of the medical image diagnosis apparatus, a physical arrangement of the plurality of monitors with respect to each of the monitors so that a first monitor is positioned to superpose a second monitor, thereby rendering the second monitor at least partially unviewable from any viewing angle.

15. A method of arranging a plurality of monitors which display a medical image in a medical image diagnosis apparatus, comprising:
 detecting movement of one of a plurality of medical X-ray imaging devices away from a patient bed to a predetermined position, using at least one sensor of the medical image diagnosis apparatus; and
 automatically placing a first monitor, based on the detected movement of the one of the medical imaging devices, behind a second monitor, thereby rendering the first monitor at least partially unviewable from any viewing angle.

16. The medical image diagnostic apparatus of claim 1, further comprising the at least one sensor, the at least one sensor being a rail sensor configured to detect the movement of the one of the at least one medical X-ray imaging device to the predetermined position, the rail sensor being located at the predetermined position.

17. The medical image diagnosis apparatus of claim 1, further comprising:
 a controller configured to receive a signal from the at least one sensor indicating the movement of the one of the at least one medical X-ray imaging device to the predetermined position, and, in response, to control the mechanism to change the physical arrangement of the plurality of monitors.

18. The medical image diagnosis apparatus of claim 1, wherein the at least one medical X-ray imaging device includes
 a first X-ray imaging device and a second X-ray imaging device
 wherein the at least one sensor is a rail sensor that detects movement of the second X-ray imaging device away from or towards the patient bed.

* * * * *